United States Patent
Lee et al.

(10) Patent No.: US 7,943,369 B2
(45) Date of Patent: May 17, 2011

(54) DNA DETECTION DEVICE AND MANUFACTURING METHOD THEREOF

(75) Inventors: In Ho Lee, Yongin-si (KR); Jun Hong Min, Yongin-si (KR); Su Hyeon Kim, Seoul (KR); Chin Sung Park, Yongin-si (KR); Ah gi Kim, Yongin-si (KR); Kui Hyun Kim, Daejeon-si (KR)

(73) Assignee: Samsung Electronics Co., Ltd. (KR)

( * ) Notice: Subject to any disclaimer, the term of this patent is extended or adjusted under 35 U.S.C. 154(b) by 1287 days.

(21) Appl. No.: 11/517,090

(22) Filed: Sep. 7, 2006

(65) Prior Publication Data
US 2007/0054391 A1    Mar. 8, 2007

(30) Foreign Application Priority Data

Sep. 7, 2005 (KR) .......................... 10-2005-0083323

(51) Int. Cl.
*C12M 1/34* (2006.01)

(52) U.S. Cl. .................................. 435/287.2; 435/288.5
(58) Field of Classification Search ................ 435/288.5
See application file for complete search history.

(56) References Cited

U.S. PATENT DOCUMENTS

| 6,710,311 B2 * | 3/2004 | Villa et al. ..................... 219/521 |
| 2005/0023156 A1 * | 2/2005 | Ramsey et al. ............... 205/792 |

* cited by examiner

*Primary Examiner* — William H Beisner
(74) *Attorney, Agent, or Firm* — Cantor Colburn LLP

(57) ABSTRACT

A DNA (Deoxyribo Nucleic Acid) detection device and a manufacturing method thereof detects DNA by an electrical method without a separate process for detection by using semiconductor microfabrication techniques. The DNA detection device includes a pair of chambers formed on a semiconductor substrate for accommodating a detection sample, a channel connecting the pair of chambers and a lid covering the pair of chambers. According to the present invention, it is possible to attain a DNA detection device, which can be mass-produced from a silicon substrate by using semiconductor manufacturing technology with improved microfabrication techniques, and a manufacturing method thereof.

7 Claims, 6 Drawing Sheets

DNA DETECTION DEVICE AND MANUFACTURING METHOD THEREOF

This application claims priority to Korean Patent Application No. 10-2005-0083323, filed Sep. 7, 2005, and all the benefits accruing therefrom under 35 U.S.C. §119, the contents of which in its entirety are herein incorporated by reference.

BACKGROUND OF THE INVENTION

1. Field of the Invention

The present invention relates to a deoxyribo nucleic acid ("DNA") detection device and a manufacturing method thereof, and more particularly, to a DNA detection device which detects DNA by an electrical method without any particular process for detection by using semiconductor microfabrication techniques, and a manufacturing method thereof.

2. Description of the Related Art

Generally, the possibility of discovering and treating human genetic diseases at an early stage from extensive DNA information and its expectations are growing. Hence, a DNA detection device is being established as another sensor in the field of biosensors.

In an attempt to directly detect DNA without performing a DNA deformation process, University of California, Santa Cruz ("UCSC") in the U.S.A. devised a structure using alpha-hemolysin, which enables DNA detection without a separate detection process, such as DNA labeling.

In addition, using such characteristics as the electrical conductivity of a DNA double helical structure, a technique of electrically detecting DNA passing through a pore formed in a membrane on a solid semiconductor substrate was intensively devised in the late 1990's at Harvard and Princeton Universities, both in the U.S.A., and at Delft University, in the Netherlands.

FIG. 1 is a cross-sectional view showing a conventional DNA detection device developed at Delft University of the Netherlands.

As shown in FIG. 1, the conventional DNA detection device has a membrane 12 on a semiconductor substrate 10 in which a pore 11 is formed.

This DNA detection device is a device capable of detecting DNA passing through the pore 11 by applying a certain electrical signal to both ends of the pore 11.

However, such conventional DNA detection devices are manufactured one by one using ion beams after manufacturing the membrane 12 by forming an insulating film on the semiconductor substrate 10, thereby rendering the process complicated and the production difficult.

Moreover, it is inconvenient to handle the membrane 12 because of its thin thickness, and also difficult to detect a signal using measuring equipment because the dwell time during which DNA passes through the pore 11 is short, which imposes many limitations in detecting DNA smoothly.

To solve these drawbacks, another prior art DNA detection device that makes measurement easier by increasing the dwell time of DNA was devised by Omar A. Saleh and Lydia L. Sohn and is disclosed in Nano Letters, 2003.

FIG. 2 is a cross-sectional view of a conventional DNA detection device.

As shown in FIG. 2, the conventional DNA detection device includes a substrate 30 made of glass, an electrode 31 formed on the substrate 30, and an upper panel 40 made of synthetic rubber, for example, polydimethylsilixane ("PDMS") having a projection.

The conventional DNA detection device has a structure in which a channel 50 is formed between the projection and the substrate 30 to detect a DNA 20 as an electrical signal from a detection sample infused between the substrate 30 and the upper panel 40.

However, the conventional DNA detection device has great difficulties in continuously producing the same structure because it is manufactured from synthetic rubber by using a mold master as a structural frame, formed by patterning SU8, which is a photoresist commercially available from Microchem Corporation, in an e-beam method.

However, the width of the channel formed 50 by the e-beam process is large, e.g., about 200 nm. Further, the method of adjusting the width of the channel 50 is restricted to the e-beam process, thus sustaining a difficulty in detecting an electrical signal of DNA passing through the wide channel, which fails to obtain a reliable result of DNA detection.

BRIEF SUMMARY OF THE INVENTION

Accordingly, the present invention is presented to solve the above-mentioned problems raised in the prior art, and an aspect, feature or advantage of the present invention is to provide a DNA detection device, which can easily detect DNA using only an electrical signal, without any particular process for detection, such as DNA labeling, by having a channel of a small enough nano size, and a manufacturing method thereof.

Another aspect, feature or advantage of the present invention is to provide a DNA detection device, which can be easily mass-produced by using improved semiconductor microfabrication techniques, and a manufacturing method thereof.

Still another aspect, feature or advantage of the present invention is to offer a DNA detection device, which can measure an electrical signal of DNA with sufficient accuracy by acquiring the reliability of measurement, and a manufacturing method thereof.

To accomplish the above aspects, features and advantages, according to one exemplary embodiment of the present invention, a DNA detection device includes: a pair of chambers formed on a semiconductor substrate for accommodating a detection sample; a channel connecting the pair of chambers; and a lid covering the chambers.

The DNA detection device may be characterized in that the channel is a path buried in an insulating film formed on the semiconductor substrate, and the surfaces of the pair of chamber are coated with the insulating film.

The DNA detection device may be characterized in that the pair of chambers is arranged symmetrically with respect to the channel, and both ends of the pair of chambers are extended so that the detection sample can be dropped between said both ends of the pair of chambers.

The DNA detection device may be characterized in that both ends of the chambers are exposed and the lid is made of one of a group of glass, PDMS and plastic.

According to another exemplary embodiment of the present invention, a manufacturing method of a DNA detection device is provided. The method includes: forming a first insulating film on the entire surface of a semiconductor substrate; etching the first insulating film by a photoetching process and etching the semiconductor substrate to a first depth to form a first pattern; etching the first insulating film by a photoetching process and etching the semiconductor substrate to a second depth greater than the first depth to form a second pattern connected to both ends of the first pattern; depositing a second insulating film on the entire surface of the oxidized semiconductor substrate to form a channel buried within the first pattern; planarizing the entire surface of the semiconductor substrate to flatten the upper part of the channel; and forming a lid on the second pattern.

The manufacturing method of a DNA detection device may be characterized in that it further includes reducing a width of the first pattern after the step of forming the second pattern.

The manufacturing method of a DNA detection device may be characterized in that the semiconductor substrate within the first pattern is oxidized or a third insulating film is deposited on a sidewall of the first pattern in order to reduce the width of the first pattern.

The manufacturing method of a DNA detection device may be characterized in that the second pattern is a pair of chambers connected by the first pattern.

The manufacturing method of a DNA detection device may be characterized in that the lid is made of one of a group of glass, PDMS and plastic.

The manufacturing method of a DNA detection device may be characterized in that the forming the lid on the second pattern is carried out by one of an anodic bonding method, a PDMS bonding method and a bonding method using a plastic patch.

The manufacturing method of a DNA detection device may be characterized in that the lid exposes both ends of the second pattern and partially covers the second pattern.

According to still another exemplary embodiment of the present invention, a manufacturing method of a DNA detection device is provided. The method includes: forming a first insulating film on an entire surface of a semiconductor substrate; etching the first insulating film by a photoetching process and forming a pair of chambers as a first pattern formed by etching the semiconductor substrate to a first depth; etching the first insulating film by a photoetching process and etching the semiconductor substrate to a second depth less than the first depth to form a second pattern connecting the pair of chambers; depositing a second insulating film on the entire surface of the oxidized semiconductor substrate to form a channel buried within the second pattern; planarizing the entire surface of the semiconductor substrate to flatten the upper part of the channel; and forming a lid on the second pattern.

The manufacturing method of a DNA detection device may be characterized in that it further includes reducing a width of the second pattern after forming the second pattern.

The manufacturing method of a DNA detection device may be characterized in that the semiconductor substrate within the first pattern is oxidized or a third insulating film is deposited on a sidewall of the second pattern in order to reduce the width of the second pattern.

BRIEF DESCRIPTION OF DRAWINGS

The above and other aspects, features and advantages of the present invention will become apparent from the following description of exemplary embodiments taken in conjunction with the accompanying drawings, in which.

DETAILED DESCRIPTION OF THE INVENTION

Figure 1:
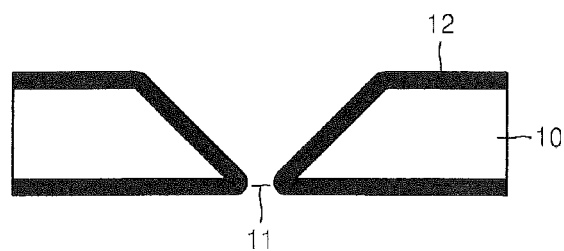
FIG. 1 is a cross-sectional view showing a conventional DNA detection device developed at Delft University of the Netherlands.
Figure 2:
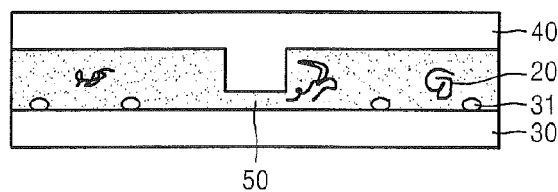
FIG. 2 is a cross-sectional view of another conventional DNA detection device according to the prior art.

The present invention now will be described more fully hereinafter with reference to the accompanying drawings, in which exemplary embodiments of the present invention are shown. The present invention may, however, be embodied in many different forms and should not be construed as limited to the exemplary embodiments set forth herein. Rather, these exemplary embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another elements as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments of the present invention are described herein with reference to cross section illustrations that are schematic illustrations of idealized embodiments of the present invention. As such, variations from the shapes of the illustrations as a result, for example, of manufacturing techniques and/or tolerances, are to be expected. Thus, exemplary embodiments of the present invention should not be construed as limited to the particular shapes of regions illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present invention.

Hereinafter, the present invention will be described in more detail with reference to the accompanying drawings.

Figure 3:
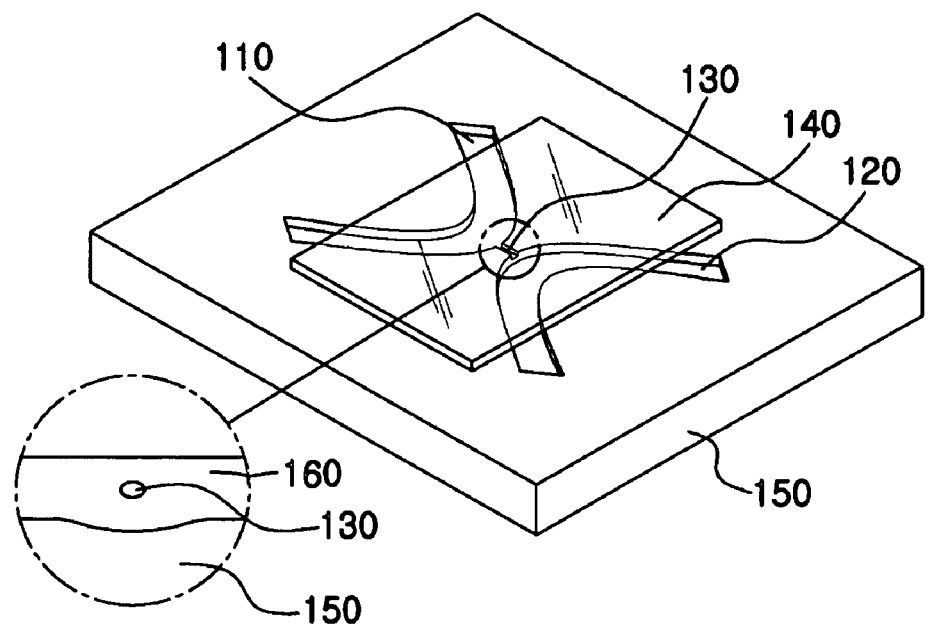
FIG. 3 is a perspective view of a DNA detection device according to an exemplary embodiment of the present invention, wherein a partial enlarged figure shown in the circle of FIG. 3 is a cross-sectional view of a channel portion.
Figure 4:
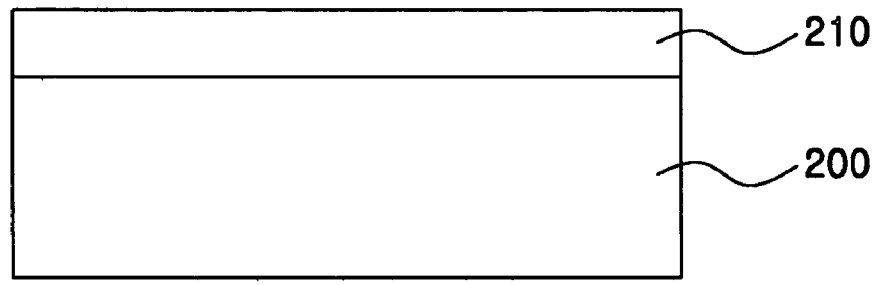
FIGS. 4 to 10 are cross-sectional views of a channel portion formed according to an exemplary manufacturing method of a DNA detection device of the present invention.

FIG. 3 is a perspective view of a DNA detection device according to an exemplary embodiment of the present invention, and a partial enlarged figure shown in the circle of FIG. 3 is a cross-sectional view of a channel portion.

As shown in FIG. 3, the DNA detection device of the present invention for detecting DNA using an electrical method includes a pair of chambers 110 and 120, a channel 130, a lid 140 and a semiconductor substrate 150.

The pair of chambers 110 and 120 has the shape of a groove formed by etching the semiconductor substrate 150, and serves as a container for accommodating a detection sample therein. Preferably, the semiconductor substrate 150 is made of a silicon substrate having improved microfabrication characteristics and low cost, and the surfaces of the chambers 110 and 120 are respectively coated with an insulating film 160 (partially shown in enlarged cross-section circled portion).

The channel 130 is a path that connects the pair of chambers 110 and 120 in fluid communication on the semiconductor substrate 150, preferably, a path buried in the insulating film 160 formed on the semiconductor substrate 150. The insulating film 160 is made of a silicon oxide film or a silicon nitride film.

Both ends of the chambers 110 and 120 are extended so that the detection sample can be dropped therebetween. Thus, the detection sample supplied from one end of the chambers 110 and 120 passes through the channel 130.

For instance, the pair of chambers 110 and 120 is arranged symmetrically with respect to the channel 130, and thus, DNA passing through the channel 130 is detected from the detection sample supplied to the pair of chambers 110 and 120, regardless of the direction of the polarity of a voltage applied in order to detect DNA.

The lid 140 covers the chambers 110 and 120, and may be formed in a single piece, or in a plurality of pieces according to need. Preferably, the chambers 110 and 120 are partially covered with the lid to expose both ends of each chamber 110 and 120, as illustrated in FIG. 3, and the lid 140 is made of any one selected from a group of glass, PDMS and plastic.

To detect DNA, a voltage is applied between the pair of chambers 110 and 120 while supplying the detection sample through the exposed one end of the chambers 110 and 120, thereby detecting DNA passing through the channel 130.

The following is a detailed description of a manufacturing method of a DNA detection device according to another exemplary embodiment of the present invention.

FIGS. 4 to 10 are cross-sectional views of a channel portion formed according to the exemplary manufacturing method of a DNA detection device of the present invention. FIG. 11 is a perspective view showing a configuration of a DNA detection device completed according to the exemplary manufacturing method of a DNA detection device of the present invention.

As shown in FIGS. 4 to 11, first, a first insulating film 210 is formed on an entire surface of a semiconductor substrate 200. It is preferable that the semiconductor substrate 200 is made of a silicon substrate having improved microfabrication characteristics and low cost, and the first insulating film 210 is formed with a silicon oxide film or silicon nitride film.

Figure 5:
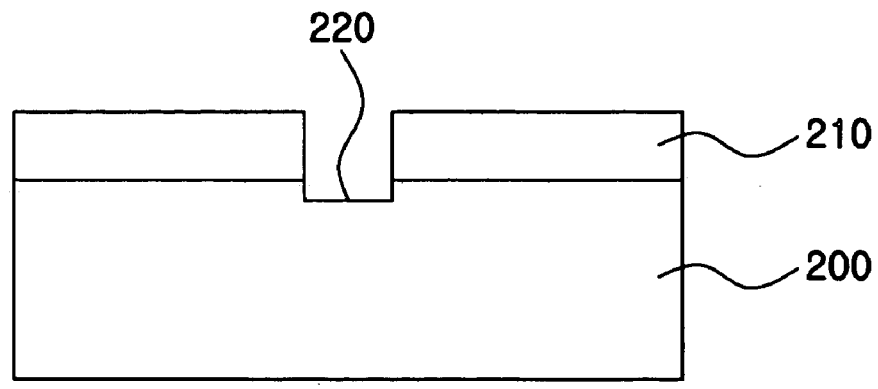
Figure 6:
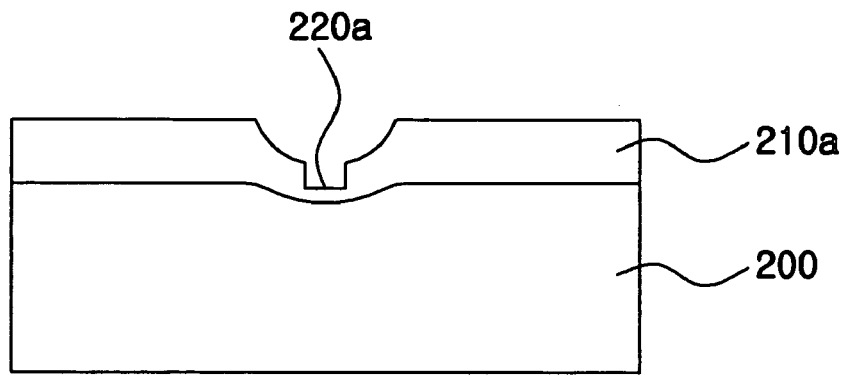

Next, as illustrated in FIG. 5, a channel photoresist pattern (not shown) for forming a channel shape is formed on the first insulating film 210 by conducting a first exposure process, and then, the first insulating film 210 and the semiconductor substrate 200 are etched by using the channel photoresist pattern as a mask. As depicted in FIG. 6, the semiconductor substrate 200 is etched to a first depth, and the channel photoresist pattern is removed to form a channel pattern 220 in the first insulating film 210 on the etched semiconductor substrate 200.

Preferably, the width of the channel photoresist pattern is made to have a nano size, as small a size as possible, by using exposure equipment.

Next, a chamber photoresist pattern (not shown) for forming a chamber shape is formed on the first insulating film 210 by performing a second exposure process, and the first insulating film 210 and the semiconductor substrate 200 are etched. In this process, the semiconductor substrate 200 is etched to a second depth, which is greater than the first depth, and the chamber photoresist pattern is removed to form a chamber pattern (not shown) on the etched semiconductor substrate.

The above chamber pattern includes, as shown in FIG. 11, a pair of chambers 280 and 290 connected to both ends of a channel 250, respectively.

Preferably, the pair of chambers 280 and 290 is formed symmetrically with respect to the channel 250.

It is also possible to carry out the forming of the channel pattern 220 and the chamber 250 in reverse order after forming the first insulating film 210. That is, the chamber pattern is first formed, and then, the channel pattern 220 connecting the pair of chambers is formed by using a photoetching process.

Next, a channel is formed at the channel pattern 220 portion. However, the step of forming a channel is varied according to whether the width of the channel pattern 220 is a small enough nano size.

If the resolution of the exposure process is not enough so that the width of the channel pattern is greater than a nano size width, reducing the width of the channel pattern 220 is additionally carried out.

Figure 7:
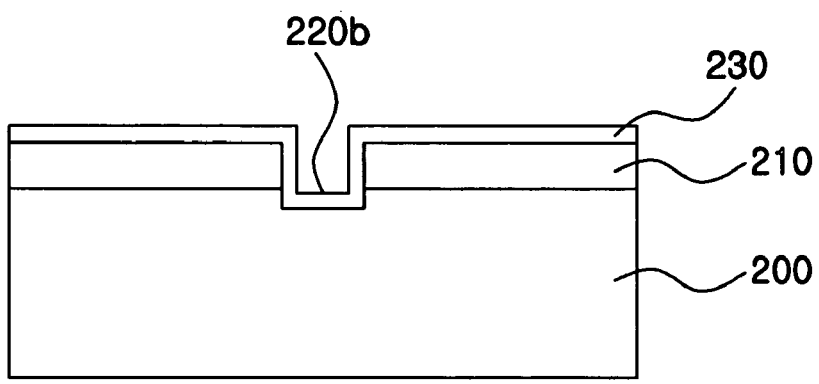

As shown in FIG. 6 or 7, the surface of the exposed semiconductor substrate 200 is oxidized in order to reduce the width of the channel pattern 220, thereby growing a silicon oxide film or a second insulating film 230 is deposited on a sidewall of the channel pattern 220. The second insulating film 230 is formed with a silicon oxide film or silicon nitride film.

Especially, in a case where the first insulating film 210 is a silicon oxide film, it is delivered as it is onto the semiconductor substrate 200 in such a shape that the width of the channel pattern 220 formed on the semiconductor substrate 200 is narrowed, as shown in FIG. 6, by an oxidation process for oxidizing the exposed semiconductor substrate 200 of the channel pattern 220, thereby forming a nano channel pattern 220a formed with a silicon oxide film. In this process, a portion where a first insulating film 210a is etched is connected to the nano channel pattern 220a in a round arc shape by the oxidation process, as illustrated in FIG. 6.

In a case where the second insulating film 230 is deposited on a sidewall of the channel pattern 220, the shape of the channel pattern 220 becomes narrowed, as depicted in FIG. 7, thereby forming a nano channel pattern 220b that is obtained by reducing the width of the channel pattern 220 to a nano size by the thickness of the second insulating film 230 formed on the sidewall of the channel pattern 220.

Figure 8:
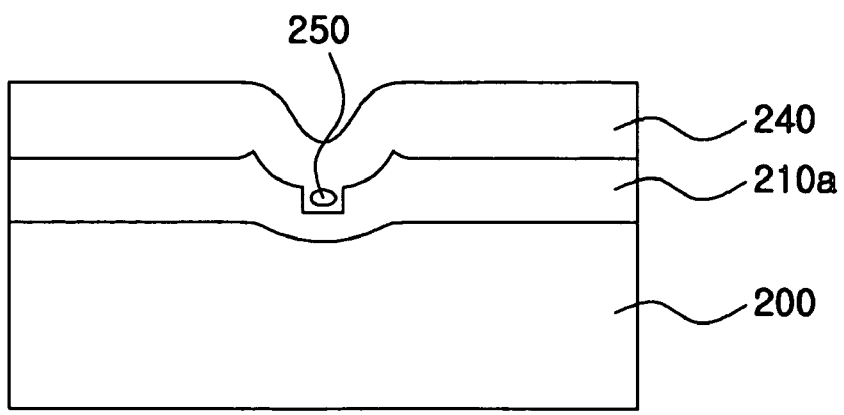

As shown in FIG. 8, a third insulating film 240 is deposited on the entire surface of the semiconductor substrate 200 having the nano channel pattern 220a (as illustrated) or 220b formed thereon, so that a space buried without being filled with the third insulating film 240 therein is left at the bottom part of the nano channel pattern 220a or 220b of a small size, thereby forming a channel 250. Preferably, the third insulating film 230 is a silicon oxide film or silicon nitride film, and deposited by a chemical vapor deposition method.

If either a plasma enhanced chemical vapor deposition ("PECVD") method or an atmospheric pressure chemical vapor deposition ("CVD") method is selected and applied as the above-mentioned chemical vapor deposition method, the third insulating film 240 is deposited in such a manner that the channel 250 is formed without filling the third insulating film 240 in the nano channel pattern 220a or 220b part of a small width because the deposited third insulating film 240 has a poor step coverage.

In order to compactly bury the upper part of the channel 250 formed within the third insulating film 240, it is preferable to deposit an insulating film by using a chemical vapor deposition method with good step coverage, for example, a low pressure chemical vapor deposition method or a chemical vapor deposition method using an organic source (not shown).

It is also advantageous to form the nano channel pattern 220a in a manner that the width thereof abruptly decreases as shown in FIG. 6 in order to easily form the shape of the channel 250 as shown in FIG. 8. Thus, in order to reduce the width of the channel pattern 220, it is preferable to grow a silicon oxide film on the channel pattern 220 by oxidizing the surface of the semiconductor substrate 200.

Figure 9:
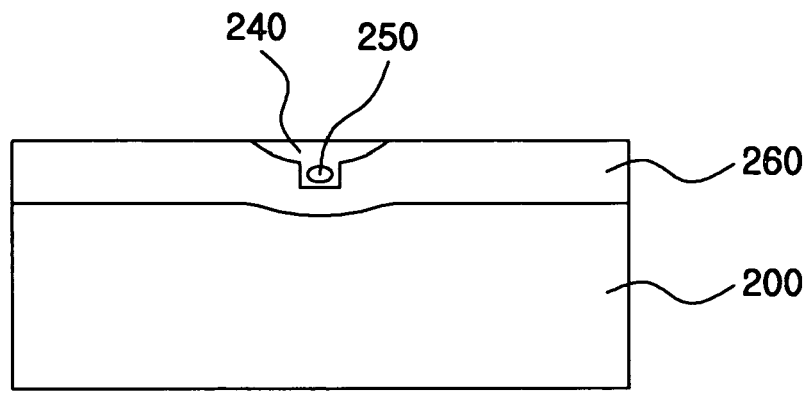
Figure 10:
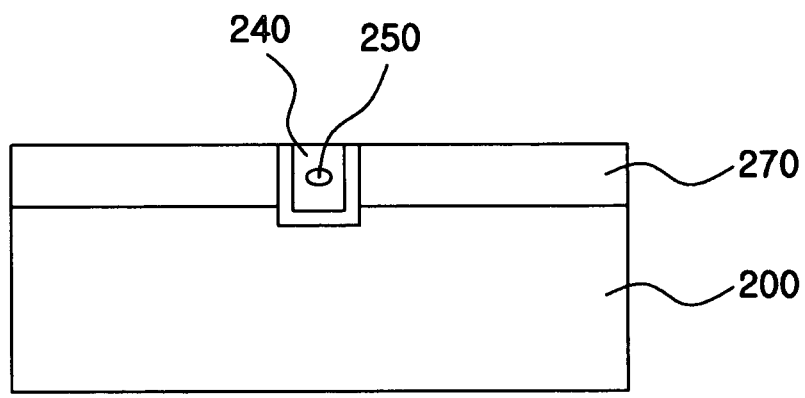
Figure 11:
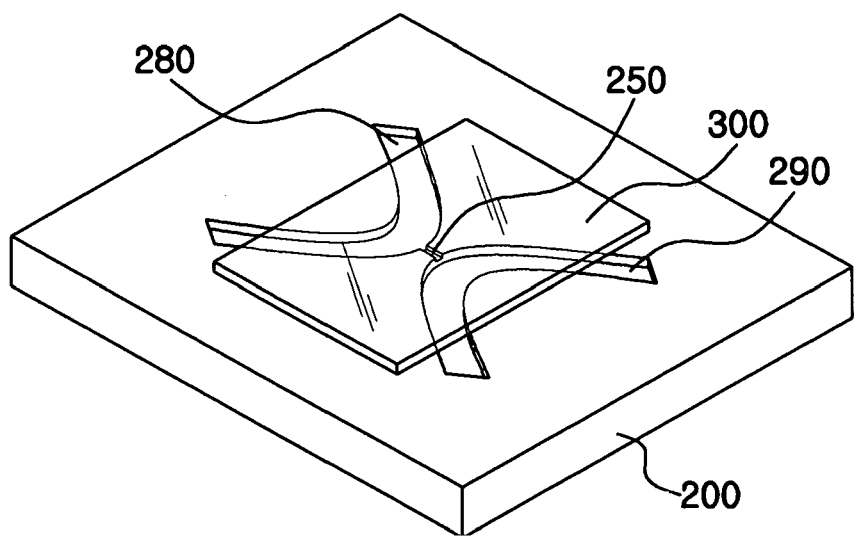
FIG. 11 is a perspective view showing a configuration of a DNA detection device completed according to the exemplary manufacturing method of a DNA detection device of the present invention.

As shown in FIGS. 9 and 10, the entire surface of the semiconductor substrate 200 is planarized by a chemical mechanical polishing technique, thereby rendering the entire surface thereof flattened. At this time, the upper part of the channel 250 is also covered flatly with the third insulating film 240.

Entire surface insulating films 260 and 270 are formed on the surfaces of other regions except for the channel 250 in which several kinds of insulating films deposited up to now are mixed and planarized. Specifically, the entire surface insulating film 260 as shown in FIG. 9 includes a thermal oxide film, and the entire surface insulating film 270 as shown in FIG. 10 has first to third insulating films mixed with each other.

Subsequently, as shown in FIG. 11, a lid 300 is formed on the flattened semiconductor substrate 200 to expose both ends of each of the pair of chambers 280 and 290. The lid 300 is made of one selected from a group of glass, polydimethylsilixane ("PDMS") and plastic. According to the material of the lid 300, it is preferable that glass is bonded to the entire insulating films 260 and 270 on the semiconductor substrate 200 using an anodic bonding method, and other materials are bonded thereto with a PDMS bonding method or a bonding method using a plastic patch.

The result of detecting DNA using the DNA detection device of the present invention is as follows. The DNA used in the experiment is 48 k lambda DNA, and a cross section of the formed channel has an elliptical shape, with a width of 120 nm, a height of 41 nm, and a channel length of 2 μm.

The DNA detection device of the present invention detects DNA passing through the channel by applying a voltage between the pair of chambers while supplying a detection sample through one exposed end of the chambers in order to detect DNA. In other words, DNA is detected by sensing a change in the amplitude of current flowing through the channel while the DNA existing in the detection sample is passing through the channel.

To be more specific, for example, when the pair of chambers and the channel are filled with a KCl solution with a concentration of 1 mole and a voltage is applied between the pair of chambers, current flows through the channel of a nano size. At this time, if DNA, which is a detection sample, is put into the chamber to which a negative voltage is applied, the DNA is moved to the chamber, to which a positive voltage is applied, through the channel because it has a negative charge.

When the DNA passes through the channel in this way, the path of the channel is reduced by the volume of the DNA, and thus, the amount of K and Cl ions flowing within the channel at a constant amount is reduced. The amount of ions thus reduced lowers the amplitude of current flowing through the channel, so that the DNA can be detected based on a change in the current measured while the DNA is passing through the channel. At this time, a degree of the change in the measured current and a sensing time are varied depending on the size and length of the DNA.

Figure 12:
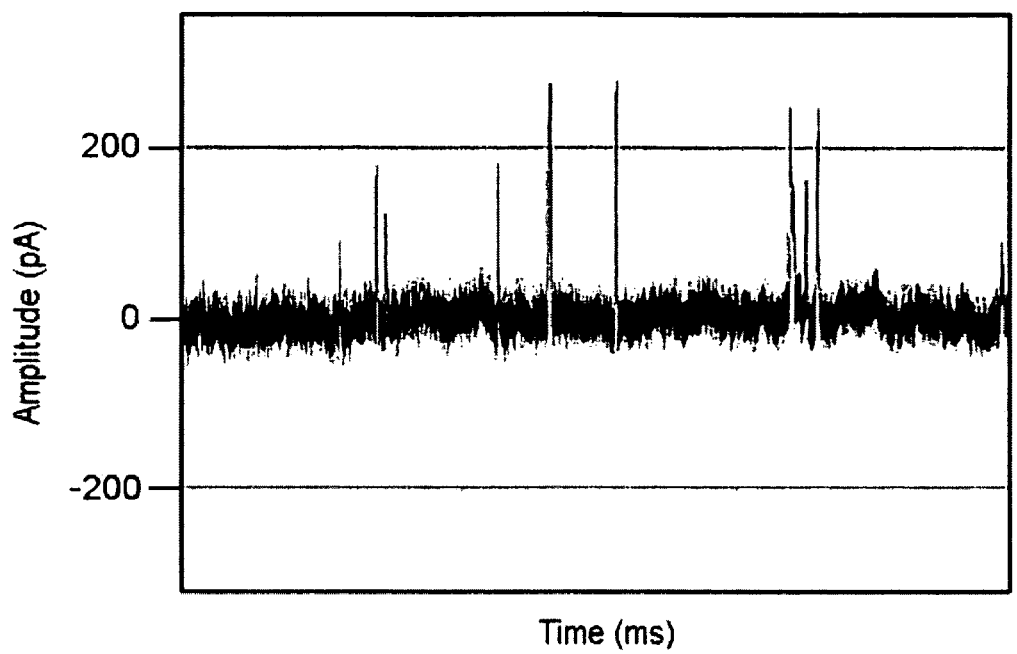
FIG. 12 is a graph showing current measured with time using a DNA detection device according to an exemplary embodiment of the present invention.

As can be known from the result of sensing a current signal above a noise level on a graph of FIG. 12 which indicates current measured with time by using the DNA detection device of the present invention, it is confirmed that the DNA passing through the channel is measured as a current signal by the DNA detection device of the present invention.

Figure 13:
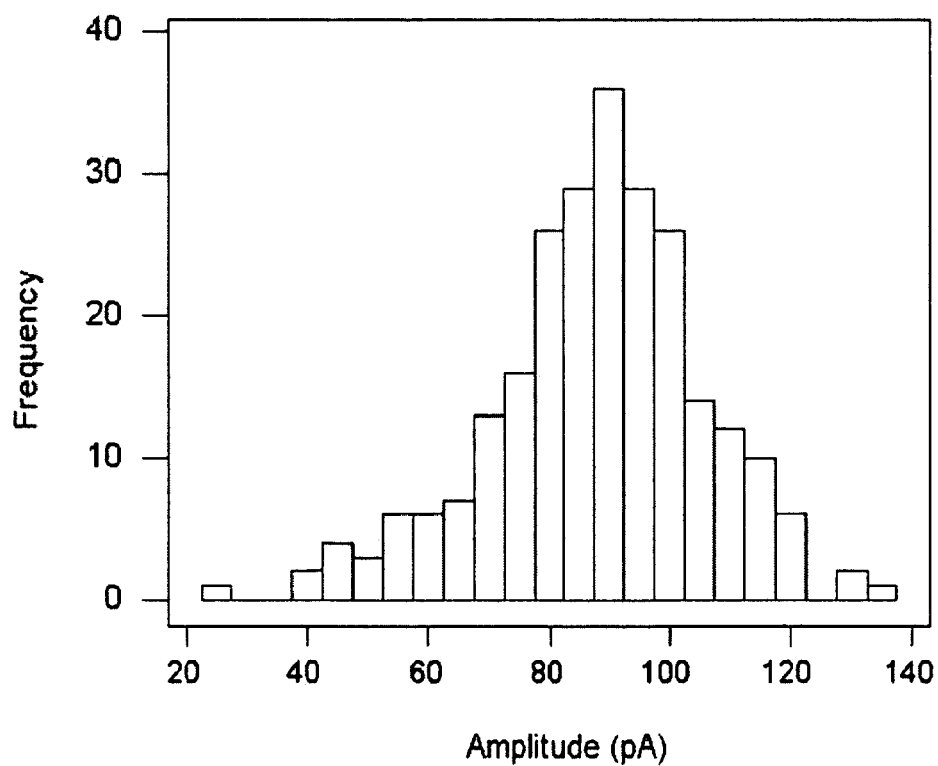
FIGS. 13 and 14 are graphs statistically showing the result of FIG. 12.
Figure 14:
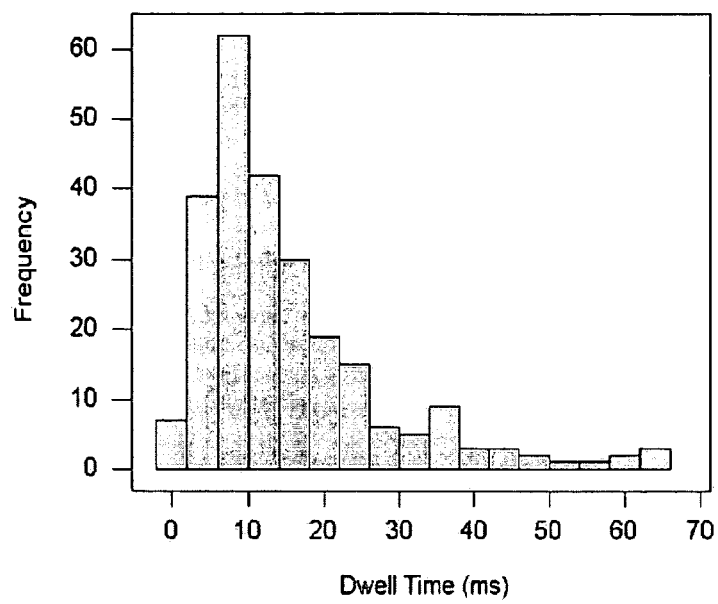

As results of FIGS. 13 and 14 statistically show the result of FIG. 12, the current signal sensed from the signal measured by the DNA detection device of the present invention exhibits a maximum frequency at an amplitude of 90 pA, and at a dwell time of 10 ms. Thus, it can be confirmed that the measurement was made with statistically sufficient repetitiveness.

Figure 15:
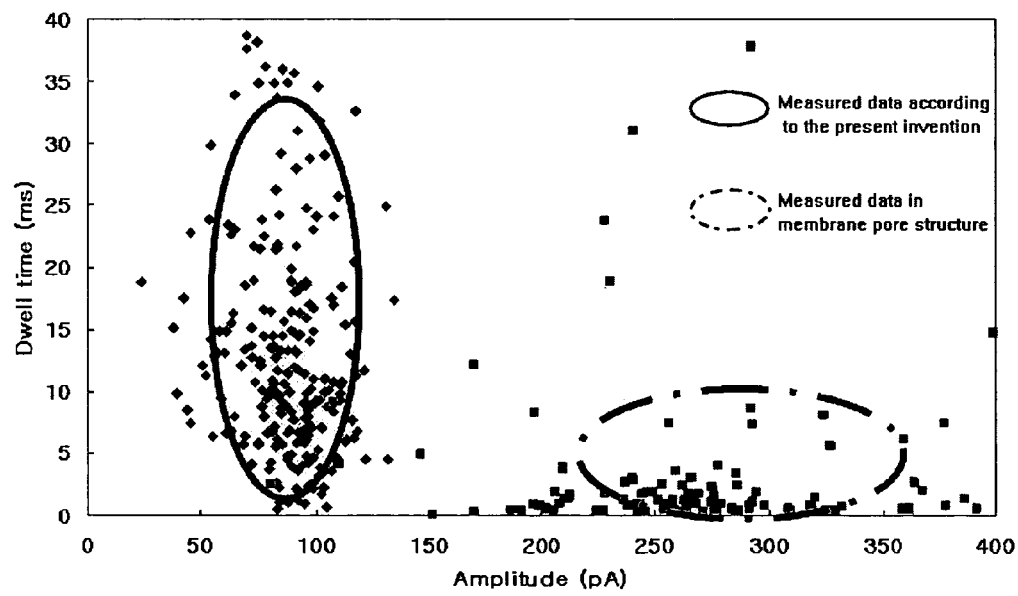
FIG. 15 is a graph showing the result obtained by a DNA detection device of an exemplary embodiment of the present invention and the result of detection characteristics of DNA detected by a conventional DNA detection device having a membrane pore structure as in FIG. 1.

FIG. 15 is a graph showing the result obtained by the DNA detection device of the present invention (e.g., FIGS. 3 and 11) and the result of detection characteristics of DNA detected by a conventional DNA detection device having a membrane pore structure, as in FIG. 1. Although, in the DNA detection device of the present invention, the amplitude of the current signal is about 100 pA, which is reduced about three times compared to 300 pA of the conventional device, it is large enough to be sensed by the measuring equipment, so there is no difficulty in such measurement.

Further, the dwell time sensed while the DNA is passing through the channel is measured to be 10 ms by the DNA detection device of the present invention, which is at least ten times greater than a dwell time measured to be 1 ms of the conventional device, thereby enabling the DNA detection device of the present invention to stably sense the dwell time with sufficient accuracy through the current measuring equipment.

As described above, the following effects are attained according to the DNA detection device and its manufacturing method of the present invention.

First, the present invention can achieve a DNA detection device, which can be mass-produced from a silicon substrate by using semiconductor manufacturing technology with improved microfabrication techniques, and a manufacturing method thereof.

Furthermore, the manufacturing method of the DNA detection device according to the present invention can easily form a channel of a nano size by employing an exposure technique and a method of reducing the width of the channel.

Accordingly, with the channel having a nano size, it is possible to detect an electrical signal with a signal amplitude and with enough time accuracy to detect DNA, without any particular process for DNA detection.

While the present invention has been shown and described with respect to particular exemplary embodiments, it will be apparent to those skilled in the art that many changes and modifications may be made without departing from the spirit and scope of the invention as defined in the appended claims.

What is claimed is:

1. A deoxyribo nucleic acid (DNA) detection device, comprising:
    a pair of chambers formed on a semiconductor substrate for accommodating a detection sample;
    a channel connecting the pair of chambers in fluid communication with one another; and
    a lid covering the pair of chambers,
    wherein the pair of chambers comprises:
    a first chamber having a first end portion, a second end portion and a center portion between the first and second end portions of the first chamber ; and
    a second chamber having a first end portion, a second end portion and a center portion between the first and second end portions of the second chamber,
    wherein the channel connects the center portion of the first chamber and the center portion of the second chamber with one another, and wherein a distance between the center portions of the first and second chambers is smaller than distances between the first end portions of the first and second chambers and between the second end portions of the first and second chambers.

2. The DNA detection device of claim 1, wherein the channel is a path buried within an insulating film formed on the semiconductor substrate.

3. The DNA detection device of claim 1, wherein the pair of chambers is arranged substantially symmetrically with respect to the channel.

4. The DNA detection device of claim 1, wherein the first and second end portions of the first chamber are extended so that the detection sample can be dropped between the first and second ends of the first chamber and the first and second end portions of the second chamber are extended so that the detection sample can be dropped between the first and second ends of the second chamber.

5. The DNA detection device of claim 1, wherein the surfaces of the pair of chambers are coated with an insulating film.

6. The DNA detection device of claim 1, wherein the first and second end portions of the first chamber and the first and second end portions of the second chamber are exposed.

7. The DNA detection device of claim 1, wherein the lid is made of one of a group of glass, polydimethylsilixane (PDMS) and plastic.

* * * * *